(12) United States Patent
Chai et al.

(10) Patent No.: US 9,295,400 B2
(45) Date of Patent: Mar. 29, 2016

(54) LINE-CONTACT DRY ELECTRODE

(71) Applicant: NATIONAL CHIAO TUNG UNIVERSITY, Hsinchu (TW)

(72) Inventors: Yun Chai, Hsinchu (TW); Chin-Teng Lin, Hsinchu County (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 14/856,074

(22) Filed: Sep. 16, 2015

(65) Prior Publication Data

US 2016/0000353 A1    Jan. 7, 2016

Related U.S. Application Data

(62) Division of application No. 13/917,852, filed on Jun. 14, 2013, now Pat. No. 9,186,084.

(30) Foreign Application Priority Data

Mar. 22, 2013 (TW) .............................. 102110244 A

(51) Int. Cl.
*A61B 5/0478* (2006.01)

(52) U.S. Cl.
CPC ....... *A61B 5/0478* (2013.01); *A61B 2562/0209* (2013.01)

(58) Field of Classification Search
CPC ..................................................... A61B 5/0478
USPC .......................................................... 600/383
See application file for complete search history.

(56) References Cited

U.S. PATENT DOCUMENTS

| | | | | |
|---|---|---|---|---|
| 4,967,038 A * | 10/1990 | Gevins | ............... | A61B 5/0017 600/383 |
| 5,038,782 A * | 8/1991 | Gevins | ............... | A61B 5/0017 600/383 |
| 6,201,982 B1 * | 3/2001 | Menkes | ............... | A61B 5/0478 600/383 |
| 6,381,481 B1 * | 4/2002 | Levendowski | ....... | A61B 5/0478 600/383 |
| 8,285,355 B2 * | 10/2012 | Chen | ............... | A61B 5/0478 600/383 |
| 8,548,554 B2 * | 10/2013 | Popescu | ............... | A61B 5/0478 600/383 |
| 2007/0238945 A1 * | 10/2007 | Delic | ................. | A61B 5/0478 600/383 |
| 2011/0046503 A1 * | 2/2011 | Pradeep | ............... | A61B 5/0478 600/544 |
| 2012/0190959 A1 * | 7/2012 | Hayakawa | ........... | A61B 5/0478 600/383 |
| 2015/0141788 A1 * | 5/2015 | Chi | ..................... | A61B 5/6803 600/383 |

* cited by examiner

*Primary Examiner* — Lee S Cohen
(74) *Attorney, Agent, or Firm* — Rosenberg, Klein & Lee

(57) ABSTRACT

A line-contact dry electrode comprises a conductive electrode base and at least one conductive contact member extending from the conductive electrode base. The conductive contact member includes a plurality of elastic conductive branches arranged intermittently to form a comb-like electrode able to comb and push away the testee's hair and contact the testee's skin.

6 Claims, 5 Drawing Sheets

LINE-CONTACT DRY ELECTRODE

RELATED APPLICATIONS

This application is a Divisional patent application of co-pending application Ser. No. 13/917,852, filed on 14 Jun. 2013, now U.S. Pat. No. 9,186,084. The entire disclosure of the prior application Ser. No. 13/917,852 is considered a part of the disclosure of the accompanying Divisional application and is hereby incorporated by reference.

BACKGROUND OF THE INVENTION

1. Field of the Invention

The present invention relates to a line-contact dry electrode, particularly to a comb-like line-contact dry electrode.

2. Description of the Related Art

In recent years, electro-biomedical signal measurement devices, which can detect physiological signals from skin, have been extensively used in medical diagnosis and research, including electrocardiography (ECG), electroencephalography (EEG), electromyography (EMG), galvanic skin reflex (GSR), and body fat meters. The electro-biomedical signal measurement devices are non-invasive detectors. For an example, EEG can record brainwaves and features economy, safety, easy operation, and comfortable inspection environment. Therefore, EEG has been widely used in clinic diagnosis and neurobiological research, such as inspections for patients of coma, apoplexy, epilepsy, encephalitis, Parkinson's disease, and other brain diseases.

The sensor electrodes used by EEG may be categorized into the wet electrodes and the dry electrodes. While the wet electrode is used, the testee's skin normally needs processing beforehand, such as removing the horny layer or shaving the hair-rich region, so as to overcome too high interface impedance between the skin and the electrode. Further, conductive paste is applied to the testee's skin to achieve better measurement quality. With time elapsed, the conductive paste will dry, and its conductivity will decay. Therefore, the conductive paste needs applying to the testee's skin repeatedly, which not only may irritate the testee's skin but also makes the operation complicated and time-consuming. The dry electrode is fabricated with a microelectromechanical technology and less likely to damage in measurement. The dry electrode normally uses a flat probe module to contact the testee's skin and detect the physiological signals without using any conductive paste. The dry electrode can directly contact the skin of a hair-rich region, e.g. the head skin. The dry electrode outperforms the wet electrode in some respects. However, the flat probe module is unlikely to comply with the contour of the head. Further, hair is likely to interfere with measurement and affect the precision thereof. Thus, the dry electrode can not effectively work in EEG, which is undertaken on the head. Therefore, how to decrease the discomfort the dry electrode causes to testees and increase the precision of measurement using the dry electrode is a problem the field concerned is eager to overcome.

SUMMARY OF THE INVENTION

The primary objective of the present invention is to provide a line-contact dry electrode, which is an elastic comb-like electrode able to comb and push away the testee's hair and closely contact the head skin, whereby is promoted precision of physiological signal measurement.

A further objective of the present invention is to provide a line-contact dry electrode, which is simple-structured and bendable, and which applies to soft EEG caps and hard EEG caps, whereby is promoted the application flexibility thereof.

To achieve the abovementioned objectives, the present invention proposes a line-contact dry electrode, which comprises a conductive electrode base and at least one conductive contact member, wherein the conductive contact member has a plurality of elastic conductive branches arranged intermittently to form a comb-like electrode able to comb and push away the testee's hair and contact the head skin. The elastic conductive branches can comply with the contour of the head and closely contacts the head skin. Thereby, physiological signals can be measured more accurately.

Each individual electrode of the present invention corresponds to a single signal channel. The branches of an electrode of the present invention can be respectively adjusted to contact the testee's skin closely, whereby the testee can wear the electrode comfortably during a long interval of test, and whereby is lowered interference on measurement.

Below, embodiments are described in detail to make easily understood the objectives, technical contents, characteristics and accomplishments of the present invention.

DETAILED DESCRIPTION OF THE INVENTION

In order to realize precision, comfortable and painless EEG measurement, the present invention proposes a novel line-contact dry electrode, which is applicable to soft EEG caps and hard EEG caps and will be very helpful to medical inspection.

Figure 1:
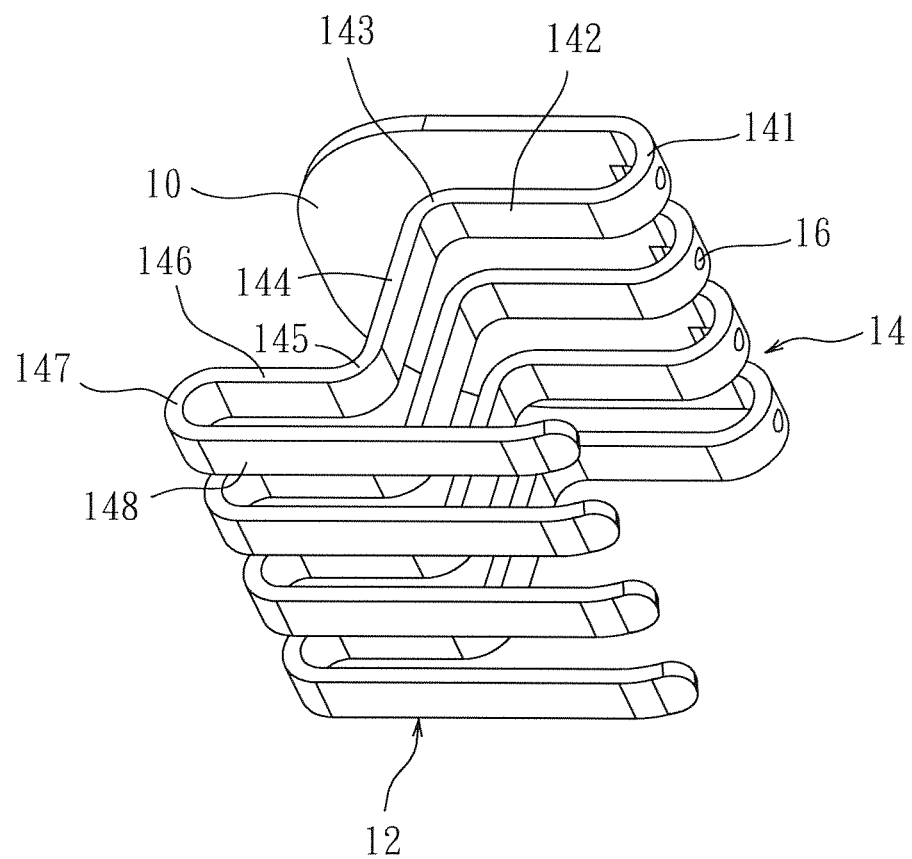
FIG. 1 schematically shows a line-contact dry electrode according to a first embodiment of the present invention.

Refer to FIG. 1 for a first embodiment of the present invention. The line-contact dry electrode of the present invention comprises a conductive electrode base 10 and at least one conductive contact member 12 extending from the conductive electrode base 10. The conductive contact member 12 includes a plurality of elastic conductive branches 14 arranged intermittently to form a comb-like electrode able to comb and push away the testee's hair and contact the testee's skin. The conductive electrode base 10 and the conductive contact member 12 are fabricated into a one-piece component. The conductive electrode base 10 and the conductive contact member 12 are preferably made of a metallic material. In the first embodiment, the conductive electrode base 10 is fabricated into a plane structure. The elastic conductive branches 14 of the conductive contact member 12 are extended from one lateral of the conductive electrode base 10, arranged intermittently, and bended at different positions successively to run downward and then horizontally. In FIG. 1, each elastic conductive branch 14 is bended from one lateral of the conductive electrode base 10 by 180 degrees to form a first camber 141. Next, the elastic conductive branch 14 is extended parallel to the conductive electrode base 10 for a distance of L1 to form a first extension 142. Next, the elastic conductive branch 14 is bended downward by 90 degrees to form a second camber 143 and then extended for a distance of H to form a second extension 144. Next, the elastic conductive branch 14 is bended upward by 90 degrees to form a third camber 145 and then extended parallel to the first extension 142 in the same extending direction of the first extension 142 for a distance of L2 to form a third extension 146. Next, the elastic conductive branch 14 is bended by 180 degrees to form a fourth camber 147 and then extended parallel to the third extension 146 but opposite to the extending direction of the third extension 146 for a distance of L3 to form a fourth extension 148, which is parallel to the conductive electrode base 10. The terminal of each elastic conductive branch 14 is bended upward to have a curve corresponding to the first bended region (such as the first camber 141).

The reasons why the elastic conductive branches 14 are bended in the abovementioned way are that the elastic fourth extensions 148 can comb and push away the testee's hair, flexibly adapt to the contour of the head skin, and closely contact the head skin and that the curves of the terminals of the elastic conductive branches 14 can prop again the head skin smooth and easily without pain. Thus is overcome the problem that the terminals of the conventional electrodes are likely to prick and hurt the head skin of testees. The hair combed and pushed by the elastic conductive branches 14 along the spacings between the elastic conductive branches 14 will be accommodated in the spaces formed by the conductive electrode base 10, the first extensions 142, the second extensions 144 and the third extension 146 without entanglement. In one embodiment, the adaptability of the dry electrode is increased via modifying the structure of the dry electrode. For example, each elastic conductive branch 14 is perforated to have a hole 16, whereby is decreased the compression on the elastic conductive branches 14, increased the overall toughness of the dry electrode, and prolonged the service life of the dry electrode. The present invention does not constrain that the conductive contact member 12 must be bended in the abovementioned way. All the dry electrodes whose conductive contact member is bended at different positions successively to form a comb-like electrode adaptable to various contours of the head are to be included within the scope of the present invention.

Figure 2:
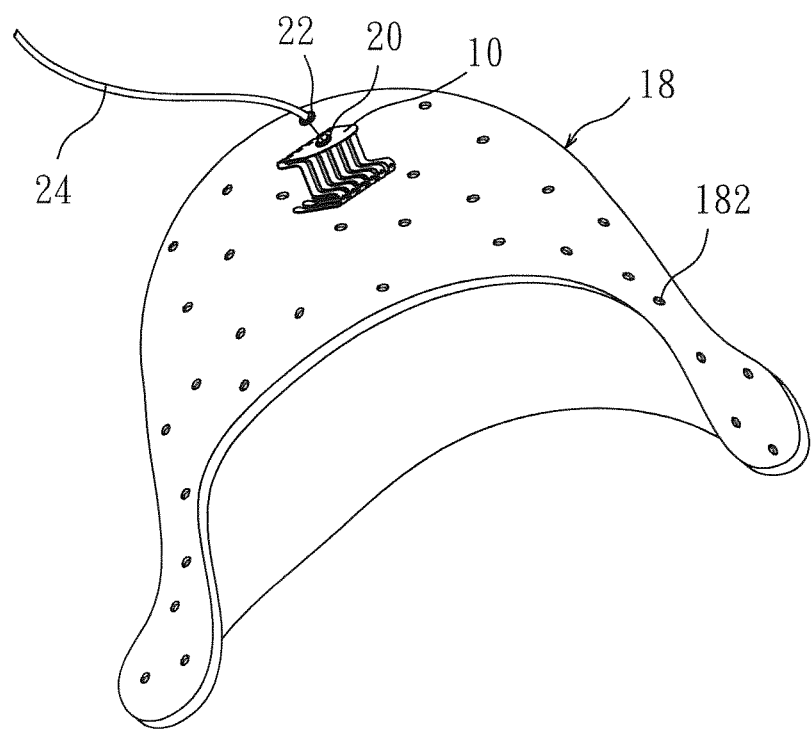
FIG. 2 schematically shows an application of a line-contact dry electrode to an EEG cap according to one embodiment of the present invention.

Refer to FIG. 1 and FIG. 2. FIG. 2 schematically shows the application of a line-contact dry electrode to an EEG cap according to one embodiment of the present invention. The operator (such as medical personnel) may arranges several line-contact dry electrodes in an EEG cap 18 (such a soft EEG cap) according to requirement. The EEG cap 18 has a plurality of through-holes 182. The conductive electrode base 10 has a first fixing element 20 (such as a male fastener). A portion of the first fixing element 20 is inserted through the through-hole 182 of the EEG cap 18 for fixing the conductive electrode base 10 on the inner surface of the EEG cap 18. A second fixing element 22 (such as a female fastener) corresponding to the first fixing element 20 is press-fitted with the first fixing element 20 from the outer surface of the EEG cap 18. The first fixing element 20 and the second fixing element 22 are made of a conductive material (such as a metallic material). A signal cable 24 is connected with the second fixing element 22. After the second fixing element 22 is press-fitted with the first fixing element 20, the signal cable 24 is electrically connected with the dry electrode. In measurement, the testee wears the EEG cap 18. While compressed, the conductive electrode base 10 actuates the elastic conductive branches 14 to comply with the contour of the testee's head, push away the testee's hair, and closely contact the head skin. As long as sufficient area of the head skin is contacted by the line-contact dry electrode, the operator begins to measure the physiological signals of the testee. The physiological signals are transmitted to an external device (such as a brainwave detector) via the signal cable 24.

Figure 3:
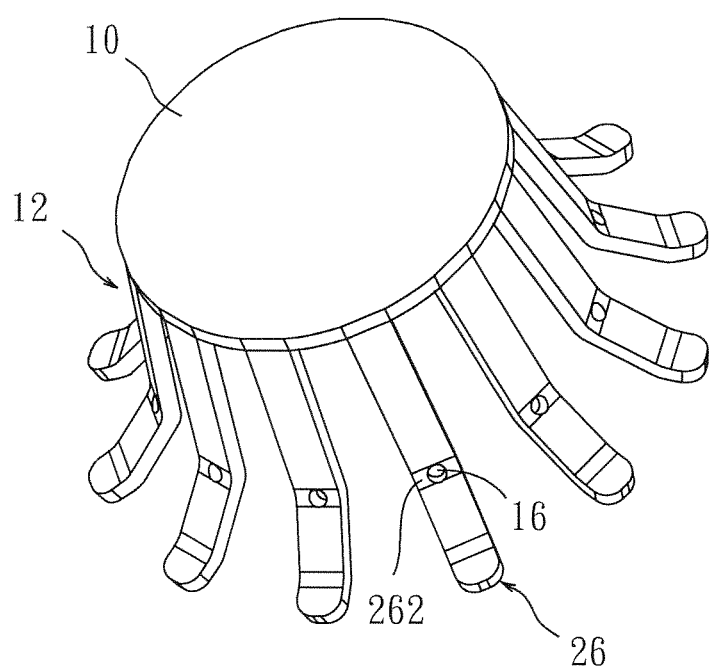
FIG. 3 schematically shows a line-contact dry electrode according to a second embodiment of the present invention.

Refer to FIG. 3 for a second embodiment. In addition to the abovementioned line-contact dry electrode with a successively-bended structure, the present invention also proposes a line-contact dry electrode with a different structure in the second embodiment. In the second embodiment, the conductive electrode base 10 is a circular-shaped plane. The elastic conductive branches of the conductive contact member 12 radiate from the circumference of the conductive electrode base 10 and extend downward vertically. Each elastic conductive branch is bended to form an L-shaped conductive contact member 26. The terminal of each L-shaped conductive contact member 26 is bended upward to have a curve. The L-shaped conductive contact member 26 has flexibility. While compressed, the flexible L-shaped conductive contact member 26 comb and push away the testee's hair radially, complying with the contour of the testee's head. The design of curving the terminal of the L-shaped conductive contact member 26 provides testees with comfortable and painless measurement. In one embodiment, a bended region 262 of each L-shaped conductive contact member 26 is perforated to have a hole 16 to increase the toughness of the elastic conductive branches and avoid the distortion of the elastic conductive branches.

Figure 4:
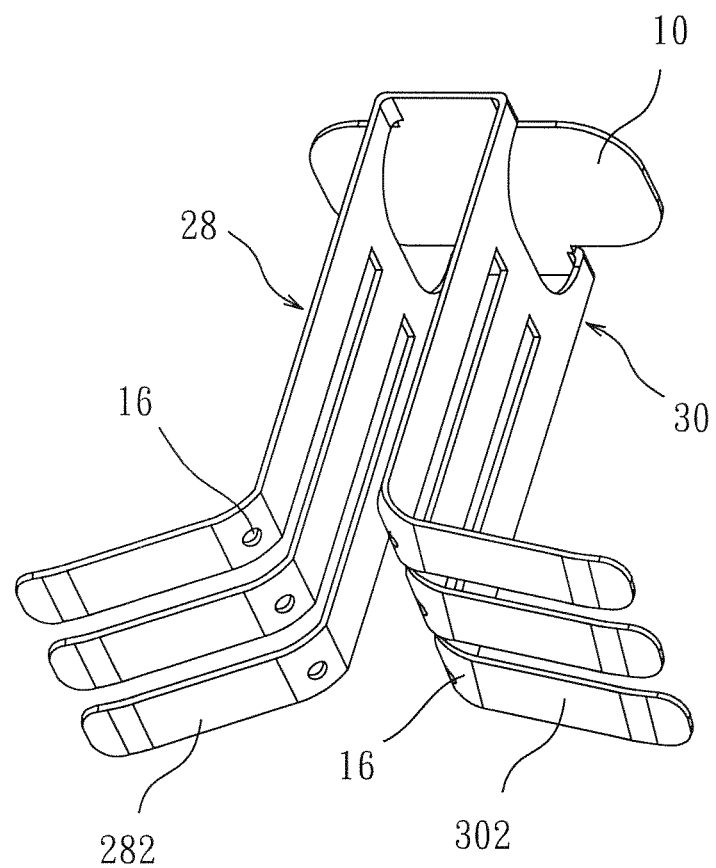
FIG. 4 schematically shows a line-contact dry electrode according to a third embodiment of the present invention.

Refer to FIG. 4 for a third embodiment. In the third embodiment, the conductive electrode base 10 is a plane structure, and there are two conductive contact members. The two conductive contact members are extended from the same face of the conductive electrode base 10 and bended downward vertically to respectively form a first L-shape conductive contact member 28 and a second L-shape conductive contact member 30. The L-shape conductive contact member 28 has a plurality of first elastic conductive branches 282. The second L-shape conductive contact member 30 has a plurality of second elastic conductive branches 302. The first L-shape conductive contact member 28 and the second L-shape conductive contact member 30 are symmetrically bended toward opposite directions. Each of the terminals of the first elastic conductive branches 282 and the second elastic conductive branches 302 is bended upward to have a curve, which makes the conductive branches slide smooth on the head skin and decreases the force applied on the head skin. While compressed, the first elastic conductive branches 282 and the second elastic conductive branches 302 respectively comb and push away the testee's hair toward opposite directions and contact the head skin, complying with the contour of the testee's head. In one embodiment, each of the bended regions of the first elastic conductive branches 282 and the second elastic conductive branches 302 is perforated to have a hole 16.

Figure 5:
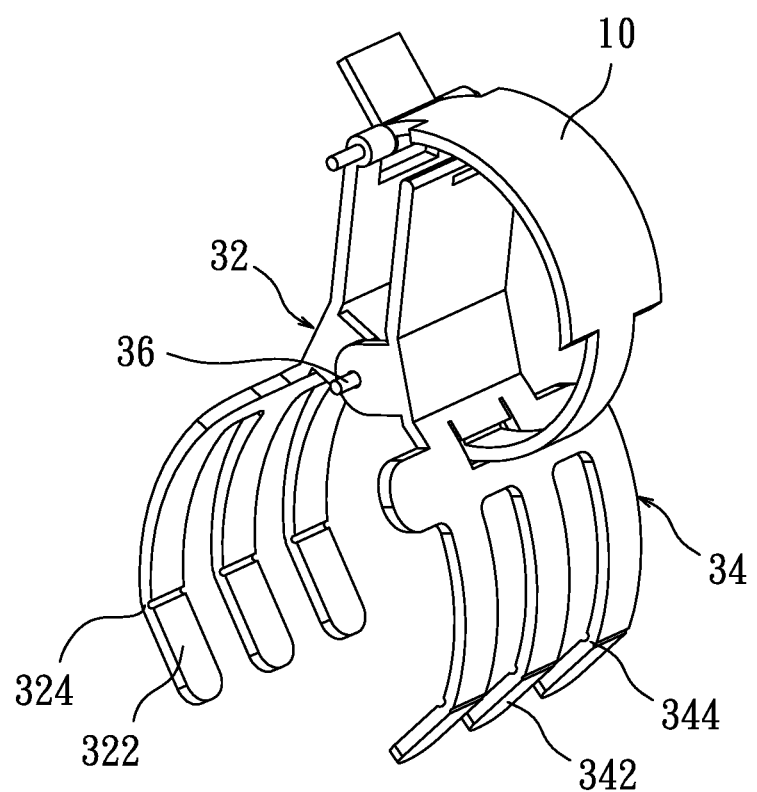
FIG. 5 schematically shows a line-contact dry electrode according to a fourth embodiment of the present invention.

Refer to FIG. 5 for a fourth embodiment. In the fourth embodiment, the conductive electrode base 10 is an arch structure, and there are two conductive contact members. The two conductive contact members are bended symmetrically to respectively form a first arch-shaped conductive contact member 32 and a second arch-shaped conductive contact member 34, which are pivotally coupled by a shaft 36. The first arch-shaped conductive contact member 32 has a plurality of first arch-shaped elastic conductive branches 322. The second arch-shaped conductive contact member 34 has a plurality of second arch-shaped elastic conductive branches 342. The first arch-shaped elastic conductive branches 322 are staggered from the second arch-shaped elastic conductive branches 342. While the conductive electrode base 10 is compressed, the first arch-shaped elastic conductive branches 322 and the second arch-shaped elastic conductive branches 342 are pivotally moved toward each other to contact each other in a staggering way, or pivotally moved far away from each other in a staggering way, with the shaft 36 being the pivotal axis. Thus, the first arch-shaped elastic conductive branches 322 and the second arch-shaped elastic conductive branches 342 comb and push away the testee's hair in opposite directions to contact at least two regions of the head skin. The present invention does not limit the application of the fourth embodiment. In fact, the structure of the fourth embodiment is applicable to hard EEG caps and soft EEG caps. Each of the terminals of the first arch-shaped elastic conductive branches 322 and the second arch-shaped elastic conductive branches 342 is bended upward to form a curve, which makes the conductive branches slide smooth on the head skin and decreases the force applied on the head skin.

In the second, third and fourth embodiments, the conductive electrode base may have a first fixing element, which can be press-fitted with a second fixing element to facilitate measurement. The installation method of the first fixing element is similar to that described in the first embodiment and will not repeat herein. The present invention is a single dry electrode corresponding to a single channel. The single dry electrode of the present invention has a plurality of branches, which deform independently under compression. In addition to being perforated to have a hole, the structure of the elastic conductive branch can also be modified via notching, which will reduce the width of the elastic conductive branch and make the elastic conductive branches deform and comply with the contour of the testee's head more easily. Alternatively, referring to FIG. 5, a thinned region 324, 344 is formed on each elastic conductive branch and has a smaller thickness than the conductive electrode base and the other part of the elastic conductive branch. As the thinned region 324, 344 is more likely to deform under compression, it increases the adaptability of the dry electrode and makes the elastic conductive branches contact the testee's skin (such as the head skin) more compliantly. Therefore, the present invention can make the testee comfortably wear the EEG cap for a long time and reduce noise in measurement. However, the present invention does not constrain the method of modifying the structure of the elastic conductive branches. Any design that can increase the compliance and adaptability of the elastic conductive branches is to be included within the scope of the present invention.

In conclusion, the present invention proposes a line-contact dry electrode, which is simple-structured and made of an elastic material having flexibility and memorability, and which is fabricated into a one-piece component, wherein the elastic comb-like electrode combs and pushes away the testee's hair to contact the testee's skin closely, whereby is promoted precision of physiological signal measurement. The present invention is applicable to soft EEG caps and hard EEG caps and adaptable in application.

The embodiments described above are only to exemplify the present invention but not to limit the scope of the present invention. Any equivalent modification or variation according to the spirit of the present invention is to be also included within the scope of the present invention, which is based on the claims stated below.

What is claimed is:

1. A line-contact dry electrode comprising a conductive electrode base and at least one conductive contact member extending from said conductive electrode base, wherein said conductive contact member includes a plurality of elastic conductive branches arranged intermittently to form a comb-like electrode able to comb and push away testee's hair and contact testee's skin;

wherein there are two said conductive contact members bent symmetrically to respectively form a first arch-shaped conductive contact member and a second arch-shaped conductive contact member, which are pivotally coupled by a shaft, and wherein said first arch-shaped conductive contact member has a plurality of first arch-shaped elastic conductive branches, and wherein said second arch-shaped conductive contact member has a plurality of second arch-shaped elastic conductive branches, and wherein said first arch-shaped elastic conductive branches are staggered from said second arch-shaped elastic conductive branches, and wherein while said conductive electrode base is compressed, said first arch-shaped elastic conductive branches and said second arch-shaped elastic conductive branches are pivotally moved toward each other to contact each other in a staggering way or pivotally moved far away from each other in a staggering way.

2. The line-contact dry electrode according to claim 1, wherein said conductive electrode base has a first fixing element adapted to be press-fitted to a second fixing element installed on a cap.

3. The line-contact dry electrode according to claim 2, wherein said first fixing element is a male fastener, and said second fixing element is a female fastener, and wherein said male fastener is adapted to be press-fitted to said female fastener.

4. The line-contact dry electrode according to claim 1, wherein a terminal of each said elastic conductive branch is bended upward to form a curve.

5. The line-contact dry electrode according to claim 1, wherein each said elastic conductive branch has a hole or a notch.

6. The line-contact dry electrode according to claim 1, wherein each said elastic conductive branch has a thinned region with a thickness smaller than that of said conductive electrode base and that of the other portion of said elastic conductive branch.

* * * * *